US012797052B2

(12) United States Patent
Nock

(10) Patent No.: US 12,797,052 B2
(45) Date of Patent: Nov. 17, 2026

(54) BIOPSY SYSTEM WITH END DEPLOY NEEDLE

(71) Applicant: Devicor Medical Products, Inc., Cincinnati, OH (US)

(72) Inventor: Andrew P. Nock, Dayton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 1086 days.

(21) Appl. No.: 17/333,285

(22) Filed: May 28, 2021

(65) Prior Publication Data

US 2021/0282754 A1 Sep. 16, 2021

Related U.S. Application Data

(63) Continuation of application No. PCT/US2019/065169, filed on Dec. 9, 2019.

(60) Provisional application No. 62/777,390, filed on Dec. 10, 2018.

(51) Int. Cl.
*A61B 10/02* (2006.01)
*A61B 90/00* (2016.01)

(52) U.S. Cl.
CPC .......... *A61B 10/0233* (2013.01); *A61B 90/39* (2016.02); *A61B 2090/3908* (2016.02)

(58) Field of Classification Search
CPC ................ A61B 10/0233; A61B 90/39; A61B 2090/3908
USPC .......................................................... 600/567
See application file for complete search history.

(56) References Cited

U.S. PATENT DOCUMENTS

| | | | | | |
|---|---|---|---|---|---|
| 4,177,797 | A * | 12/1979 | Baylis | A61B 10/025 600/567 |
| 5,665,102 | A | 9/1997 | Yoon | |
| 6,083,524 | A | 7/2000 | Sawhney et al. | |
| 6,162,241 | A | 12/2000 | Coury et al. | |
| 6,234,177 | B1 | 5/2001 | Barsch | |
| 6,270,464 | B1 | 8/2001 | Fulton, III et al. | |
| 6,356,782 | B1 | 3/2002 | Sirimanne et al. | |
| 6,605,294 | B2 | 8/2003 | Sawhney | |
| 8,600,481 | B2 | 12/2013 | Sirimanne et al. | |

(Continued)

FOREIGN PATENT DOCUMENTS

| | | | |
|---|---|---|---|
| CN | 1754512 | A | 4/2006 |
| CN | 1827050 | A | 9/2006 |

(Continued)

OTHER PUBLICATIONS

International Search Report and Written Opinion dated Feb. 27, 2020 for Application No. PCT/US2019/065169, 12 pages.

(Continued)

*Primary Examiner* — Chanel J Yoon
(74) *Attorney, Agent, or Firm* — FBT Gibbons LLP

(57) ABSTRACT

A needle for use with a biopsy device includes an outer cannula, and a tissue piercing tip. The outer cannula defines a cutter lumen for receiving a cutter therein and a lateral lumen adjacent to the cutter lumen. The tissue piercing tip has a body, a marker opening, and a marker lumen. The body defines a plurality of cutting surfaces. The marker opening is disposed on at least one cutting surface of the plurality of cutting surfaces. The marker lumen extends distally through the body from the marker opening to a proximal opening. The proximal opening is in communication with the cutter lumen.

17 Claims, 14 Drawing Sheets

(56) References Cited

U.S. PATENT DOCUMENTS

| | | | | |
|---|---|---|---|---|
| 8,939,910 | B2 | 1/2015 | Fisher | |
| 2006/0089564 | A1 * | 4/2006 | Goldenberg ....... | A61B 10/0233 600/566 |
| 2007/0038145 | A1 | 2/2007 | Field | |
| 2008/0119881 | A1 | 5/2008 | Vetter | |
| 2011/0071431 | A1 * | 3/2011 | Speeg .................... | A61B 90/39 600/567 |
| 2012/0330186 | A1 | 12/2012 | Rhad et al. | |

FOREIGN PATENT DOCUMENTS

| | | | | |
|---|---|---|---|---|
| EP | 1767167 | A2 | 3/2007 | |
| JP | 2013-539386 | A | 10/2013 | |
| JP | 2018-528827 | A | 10/2018 | |
| WO | 2007/021903 | A2 | 2/2007 | |
| WO | WO-2016201115 | A1 * | 12/2016 | ............. A61B 10/02 |

OTHER PUBLICATIONS

Chinese Office Action dated May 19, 2023 for Application No. 201980079489.7, 9 pages.
Chinese Office Action dated Oct. 13, 2023 for Application No. 201980079489.7, 14 pages.
Extended European Search Report dated Apr. 19, 2023 for Application No. 23154734.0, 6 pages.
Japanese Office Action dated Aug. 15, 2023 for Application No. 2021-532451, 11 pages.
Japanese Office Action dated Feb. 8, 2024 for Application No. 2021-532451, 8 pages.
Japanese Office Action dated Jul. 4, 2024 for Application No. 2021-532451, 8 pages.
Korean Office Action dated Aug. 27, 2024 for Application No. 10-2021-7017312, 11 pages.

* cited by examiner

BIOPSY SYSTEM WITH END DEPLOY NEEDLE

PRIORITY

This application is a continuation of International Application Number PCT/US2019/065169 entitled "Biopsy System with End Deploy Needle," filed on Dec. 9, 2019, which claims priority to U.S. Provisional Patent App. 62/777,390 entitled "Biopsy System with End Deploy Needle," filed on Dec. 10, 2018, the disclosure of which is incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

The use of markers used after breast biopsies to mark the location where the biopsied tissue was removed is described in the following US Patents: U.S. Pat. No. 6,083,524, "Polymerizable biodegradable polymers including carbonate or dioxanone linkages," issued Jul. 4, 2000; U.S. Pat. No. 6,162,241, "Hemostatic tissue sealants," issued Dec. 4, 2000; U.S. Pat. No. 6,270,464, "Biopsy localization method and device," issued Aug. 7, 2001; U.S. Pat. No. 6,356,782, "Subcutaneous cavity marking device and method," issued Mar. 12, 2002; U.S. Pat. No. 6,605,294, "Methods of using in situ hydration of hydrogel articles for sealing or augmentation of tissue or vessels," issued Aug. 12, 2003; U.S. Pat. No. 8,600,481, "Subcutaneous cavity marking device," issued Dec. 3, 2013 and U.S. Pat. No. 8,939,910, "Method for enhancing ultrasound visibility of hyperechoic materials", issued Jan. 27, 2015. All of these US Patents are incorporated by reference in their entirety.

In some contexts, a marker biopsy site marker is used to identify a biopsy site after a biopsy procedure. In some examples such biopsy site markers can be deployed at a biopsy site through a biopsy needle using a side-deploy marker delivery device. In this configuration, the marker delivery device includes a side aperture that corresponds to the side aperture of the biopsy needle. However, this configuration might not be completely satisfactory under all circumstances; yet the concept of deploying through the biopsy needle may remain desirable. Accordingly, in some contexts, it may be desirable to deploy a biopsy site marker from an end-deploy marker delivery device with the marker delivery device disposed in the biopsy needle. While several systems and methods have been made and used for marking a biopsy site, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1A:
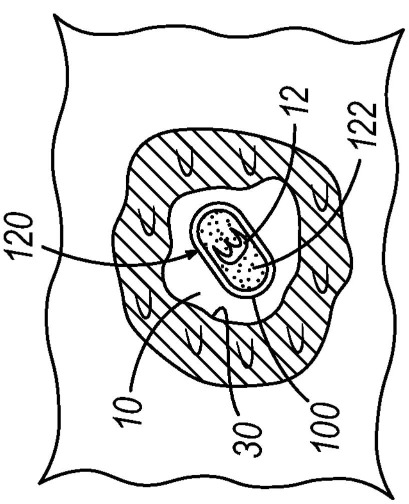
FIGS. 1A, 1B, and 1C show exemplary aspects of placement of a biopsy site marker, in accordance with aspects of the present disclosure.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

I. Exemplary Marker

Figure 1B:
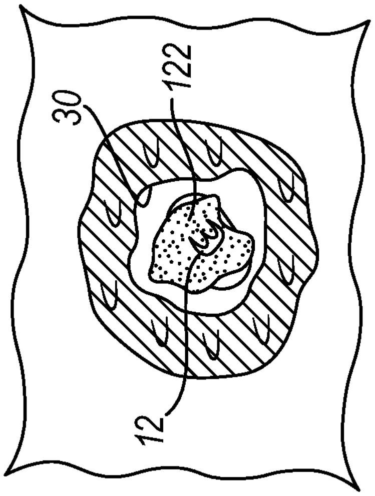
Figure 1C:
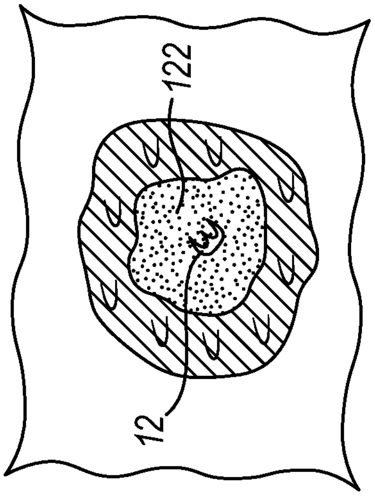

Aspects presented herein relate to devices and procedures for manufacturing a marker for percutaneously marking a biopsy cavity (10) having surrounding tissue (30), as shown in FIGS. 1A-1C. For instance, as seen in FIG. 1A, a marker (100) may be initially placed in the biopsy cavity (10) to facilitate relocation of the biopsy site. Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some examples, carrier (120) can include a plurality of microbubbles to enhance visualization of carrier (120) under ultrasound. As will be described in greater detail below, marker material (122) is generally bioabsorbable such that marker material (122) may be generally absorbed into the patient's tissue over time. In the present example, marker material (122) comprises a hydrogel that is initially in a dehydrated state. Although a hydrogel is used in the present example, it should be understood that in other examples marker material (122) may comprise other known bioabsorbable materials In the present example, marker (100) further includes a marker element (12) that is generally not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12). In still other examples, marker (100) may be formed with only marker element (12) such that carrier (120) is omitted and marker element (12) is in a "bare" form. In other words, in some examples marker (100) is formed of only carrier (120) as a bare clip.

Marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, maker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured and the natural mechanical parameters of the tissue are substantially restored to those of the pre-damaged condition.

Marker (100) may be inserted into the body either surgically via an opening in the body cavity (30), or through a minimally invasive procedure using such devices as a catheter, introducer or similar type insertion device. Marker (100) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) of the present example is large enough to be readily visible to a clinician under x-ray or ultrasonic viewing, for example; yet small enough to be able to be percutaneously deployed into the biopsy cavity and to not cause any difficulties with the patient. Although examples are described in connection with treatment and diagnosis of breast tissue, aspects presented herein may be used for markers in any internal, tissue, e.g., in breast tissue, lung tissue, prostate tissue, lymph gland tissue, etc.

The hydration of the marker material (122) of carrier (120) by the natural moisture of the tissue surrounding it causes expansion of the polymer and thus minimizes the risk of migration. The growing hydrogel based marker material (122) centers marker (100) in the biopsy cavity as it grows. As the hydrogel expands, naturally-present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of the permanent marker (12) within the hydrogel hydrated marker material (122) because the permanent marker (12) is outlined as a specular reflector within a hypoechoic hydrated marker having a water-like nonreflective substrate.

II. Exemplary Marker Delivery Device

Figure 2:
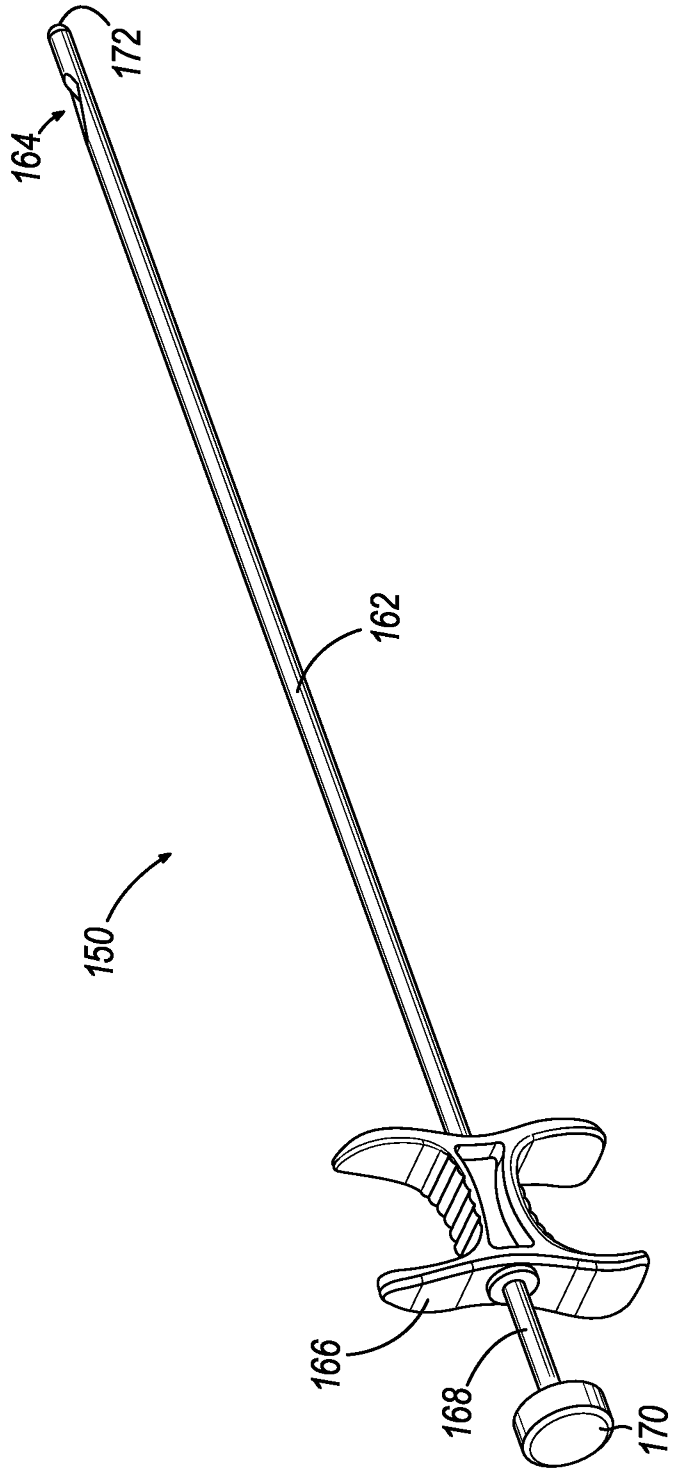
FIG. 2 depicts a perspective view of an exemplary marker delivery device.

In some examples it may be desirable to deploy marker (100) described above within the body cavity (30) using certain marker delivery devices. For instance, FIGS. 2 and 3 show an exemplary marker delivery device (150) which includes an elongate outer cannula (162) having a marker exit, such as side opening (164) formed adjacent to, but spaced proximally from, the distal end of the cannula (162).

A grip (166) can be provided at the proximal end of cannula (162). A push rod (168) can be provided, with push rod (168) extending coaxially in cannula (162) such that push rod (168) is configured to translate within cannula (162) to displace one or more markers through side opening (164) (see FIG. 3). Rod (168) may have sufficient rigidity in compression to push a marker from an internal lumen (165) of cannula (162) out through opening (164), yet be relatively flexible in bending. A plunger (170) is coupled at the proximal end of rod (168) for forcing rod (168) distally in cannula (162) to deploy a marker out of cannula (162).

A user may grasp grip (166) with two fingers, and may push on plunger (170) using the thumb on the same hand, so that marker delivery device (160) is operated by a user's single hand. A spring (not shown) or other feature may be provided about rod (168) to bias rod (168) proximally relative to grip (166) and cannula (162).

Figure 3:
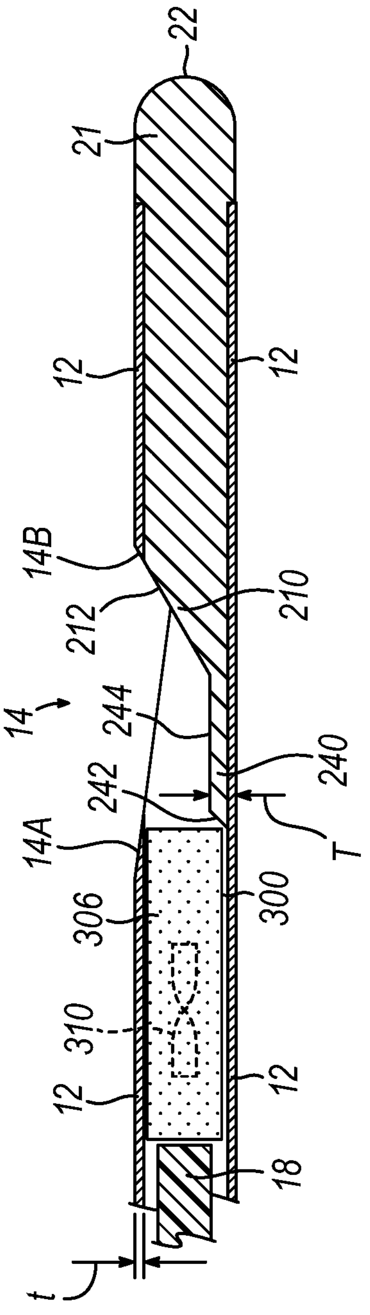
FIG. 3 depicts a side cross-sectional view of the marker delivery device of FIG. 2.

FIG. 3 shows a cross-sectional view of a distal portion of the marker delivery device (160). As can be seen, a biopsy marker (300) similar to marker (100) described above is disposed within internal lumen (165) of cannula (162). In the present example, marker (300) comprise a biodegradable or otherwise resorbable marker material (306), such as a generally cylindrically shaped body of collagen, hydrogel, or etc., and a metallic, generally radiopaque permanent marker or marker element (310) (shown in phantom) disposed within or otherwise carried by marker material (306).

Cannula (162) may be formed of any suitable metallic or non-metallic material. In some versions, cannula (162) is formed of a thin walled hollow tube formed of a suitable medical grade plastic or polymer. One suitable material is a thermoplastic elastomer, such as Polyether block amide (PEBA), such as is known under the tradename PEBAX. Cannula (162) may be formed of PEBAX, and may be substantially transparent to visible light and X-ray.

Side opening (164) may be formed by cutting away a portion of the wall of cannula (162). Side opening (164) communicates with an internal lumen (165) of cannula (162). Side opening (164) may extend axially (in a direction parallel to the axis of lumen (165)) from a proximal opening end (164A) to a distal opening end (164B), as illustrated in FIG. 3.

In the present example, distal tip (172) extends from the distal end of cannula (162) and is rounded as shown in FIG. 3. Referring to FIG. 3, the distal end of cannula (162) is closed by a unitary endpiece (171), with a portion of endpiece (171) extending into internal lumen (165) of cannula (162). Endpiece (171) may be a molded or cast component. Endpiece (171) comprises a tip (172), a ramp (210) having a ramp surface (212), and a marker engaging element (240). Ramp surface (212) aids in directing marker (300) from internal lumen (165) through side opening (164). Marker engaging element (240) helps to retain marker (300) in internal lumen (165) until the user intends to deploy marker (300).

Marker engaging element (240) is disposed within internal lumen (165), and at least a portion of marker engaging element (240) is disposed distally of proximal end (164A) of side opening (164). Marker engaging element (240) extends along a portion of the floor of cannula (162) under opening (164) such that marker engaging element (240) is positioned to reinforce the portion of cannula (162) in which opening (164) is formed. For instance, by positioning marker engaging element (240) underneath opening (164), as shown in FIG. 3, element (240) helps to stiffen cannula (162) in the region where wall of cannula (162) is cut to form opening (164). As shown in FIG. 3, marker engaging element (240) extends from the proximal most portion of ramp surface (212), and does not extend proximally of side opening (164), though in other embodiments, a portion of element (240) may extend proximally of opening (164).

As shown in FIG. 3, marker engaging element (240) is in the form of a step having a generally uniform thickness (T) along element's (240) axial length, except that element (240) has a tapered proximal end (242). Tapered proximal end (242) forms an included angle with the longitudinal axis of lumen (165) (included angle with a horizontal line in FIG. 3) of about 45 degrees, while ramp surface (212) forms an included angle with the longitudinal axis of about 30 degrees. Of course, any number of other suitable angles may be used.

As shown in FIG. 3, an upwardly facing surface (244) (surface facing opening (164)) of marker engaging element (240) extends distally to contact ramp surface (212), so that there is not a space or gap between surface (244) and ramp surface (212). Such an arrangement is advantageous to reduce the possibility that marker (300), upon moving past marker engaging element (240), may become lodged between marker engagement element (240) and ramp (212). In some versions, marker engaging element (240), ramp (210), and/or tip (172) are formed of, or include, a material that is relatively more radiopaque than the wall of cannula (162). For instance, where element (240), ramp (210), and tip (172) are formed as an integral endpiece (171), endpiece (171) may include a radiopaque additive, such as barium sulfate. For instance, endpiece (171) may be a component molded of PEBAX, with about 20 percent by weight barium sulfate added to the molten PEBAX mold composition. The relatively more radiopaque marker engaging element (240), ramp (210), and tip (22) may be useful in distinguishing the position of those components using radiographic imaging. Also, where ramp (210) and/or step of engaging element (240) are positioned in association with opening (164), the addition of a radiopaque material can help identify the position of opening (164), and the position of marker (300) relative to opening (164) before, during, or after deployment of marker (300).

Figure 4:
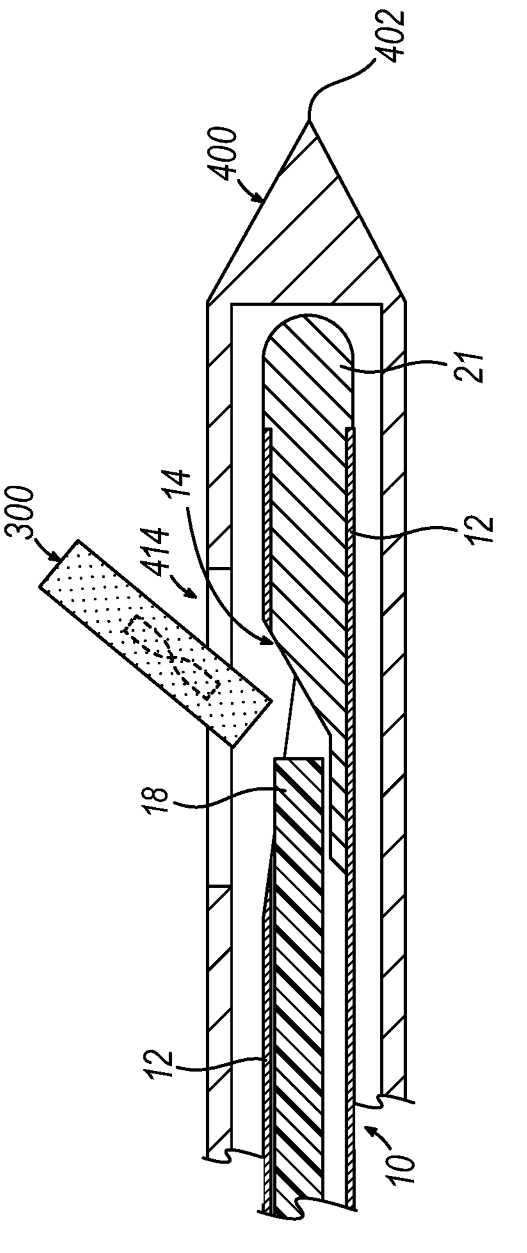
FIG. 4 depicts a cross-sectional view of a marker being deployed from the distal portion of the marker delivery device of FIG. 1 and through a lateral aperture in a biopsy needle to mark a biopsy site.
Figure 5:
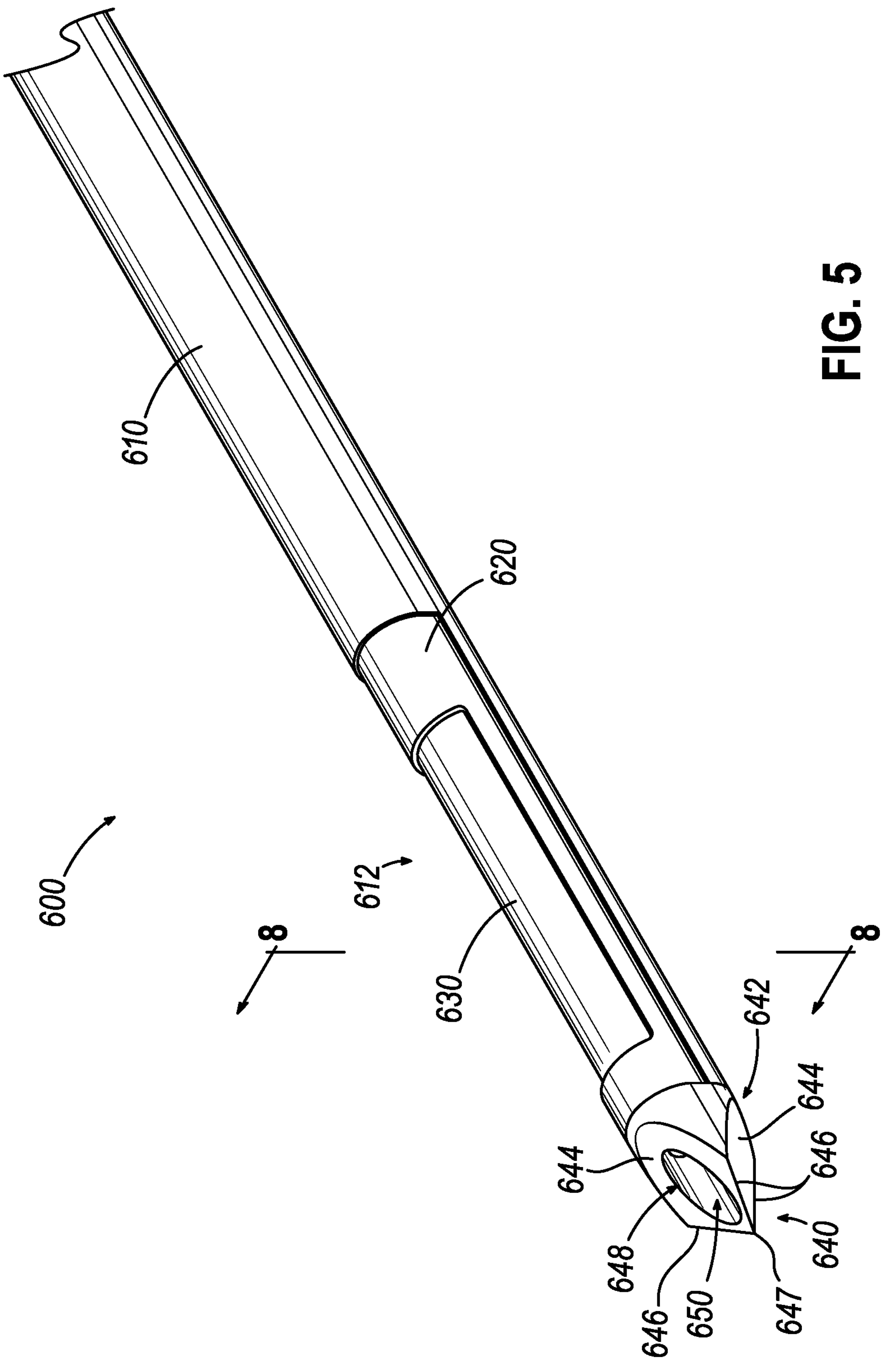
FIG. 5 depicts a detailed perspective view of an exemplary biopsy needle.

Referring to FIG. 4, marker delivery device (160) is used to deploy a marker (300) to mark a biopsy location within a patient. In FIG. 4, a cannular biopsy needle (400) is shown having a closed distal end with piercing tip (402) and a lateral tissue receiving aperture (414). Marker delivery device (160) is introduced to a biopsy site through biopsy needle (400), which may be the same needle (400) used to collect a tissue sample from the biopsy site. Biopsy needle (400) may be of the type used with single insertion, multiple sample vacuum assisted biopsy devices. Several such biopsy devices are disclosed in the various patents and patent applications that have been referred to and incorporated by reference herein, though other biopsy devices may be used.

FIG. 4 shows the distal end of marker delivery device (160) disposed within needle (400). Needle (400) may be positioned in tissue, and a biopsy sample may be obtained through lateral aperture (414), thereby providing a biopsy cavity adjacent lateral aperture (414). Then, after the tissue sample has been obtained and transferred proximally through needle (400), and without removing needle (400) from the patient's tissue, marker delivery device (160) is inserted into a proximal opening in needle (400). In FIG. 4, needle (400) and marker delivery device (160) are positioned such that opening (164) of cannula (162) and lateral aperture (414) of needle (400) are substantially aligned axially and circumferentially. Then, with marker delivery device (160) and needle (400) so positioned at the biopsy site, push rod (168) is advanced to deploy marker (300) up ramp surface (212), through opening (164), and then through lateral aperture (414), into the biopsy cavity.

III. Exemplary Biopsy System With End Deployment Feature

In some examples it may be desirable to deploy a marker similar to markers (100, 300) described above in other ways. In particular, in some examples it may be desirable to deploy a marker from the distal end of a marker delivery device similar to marker delivery device (150) described above. In such examples, deployment from the distal end may be desirable due to improved usability. For instance, when markers are deployed through an opening like side opening (164) described above, such markers may be susceptible to increased resistance from the opening (164). Moreover, in some examples a push rod similar to push rod (168) may be susceptible to engaging the opening, which could lead to increased procedure time. In examples where deployment is provided through the distal end of the marker delivery device, these challenges can be eliminated.

In examples where marker deployment is provided through the distal end of the marker delivery device, it may be desirable to incorporate features into associated devices to support such marker delivery device configurations. For instance, in examples where marking is performed through a biopsy needle, it may be desirable to include features in the biopsy needle to more readily promote maker deployment through the distal end of the marker delivery device. While various examples of suitable devices for providing marker deployment through the distal end of a marker delivery device are described herein, it should be understood that various alternative configurations may be used as will be apparent to those of ordinary skill in the art in view of the teachings herein.

A. Exemplary Biopsy Needle with Deployment Opening

FIGS. 5-8 show an exemplary biopsy needle (600) that may be used with various marker delivery devices described herein. It should be understood that unless otherwise explicitly noted herein, biopsy needle (600) is substantially similar to biopsy needle (400) described above. Biopsy needle (600) of the present example comprises an outer cannula (610), a lateral aperture (612) formed therein, and a tissue piercing tip (640) secured to the distal end of outer cannula (610). Although not shown, it should be understood that the proximal end of outer cannula (610) can be coupled to the distal end of a biopsy device (not shown) to promote the collection of tissue samples via biopsy needle (600).

Figure 8:
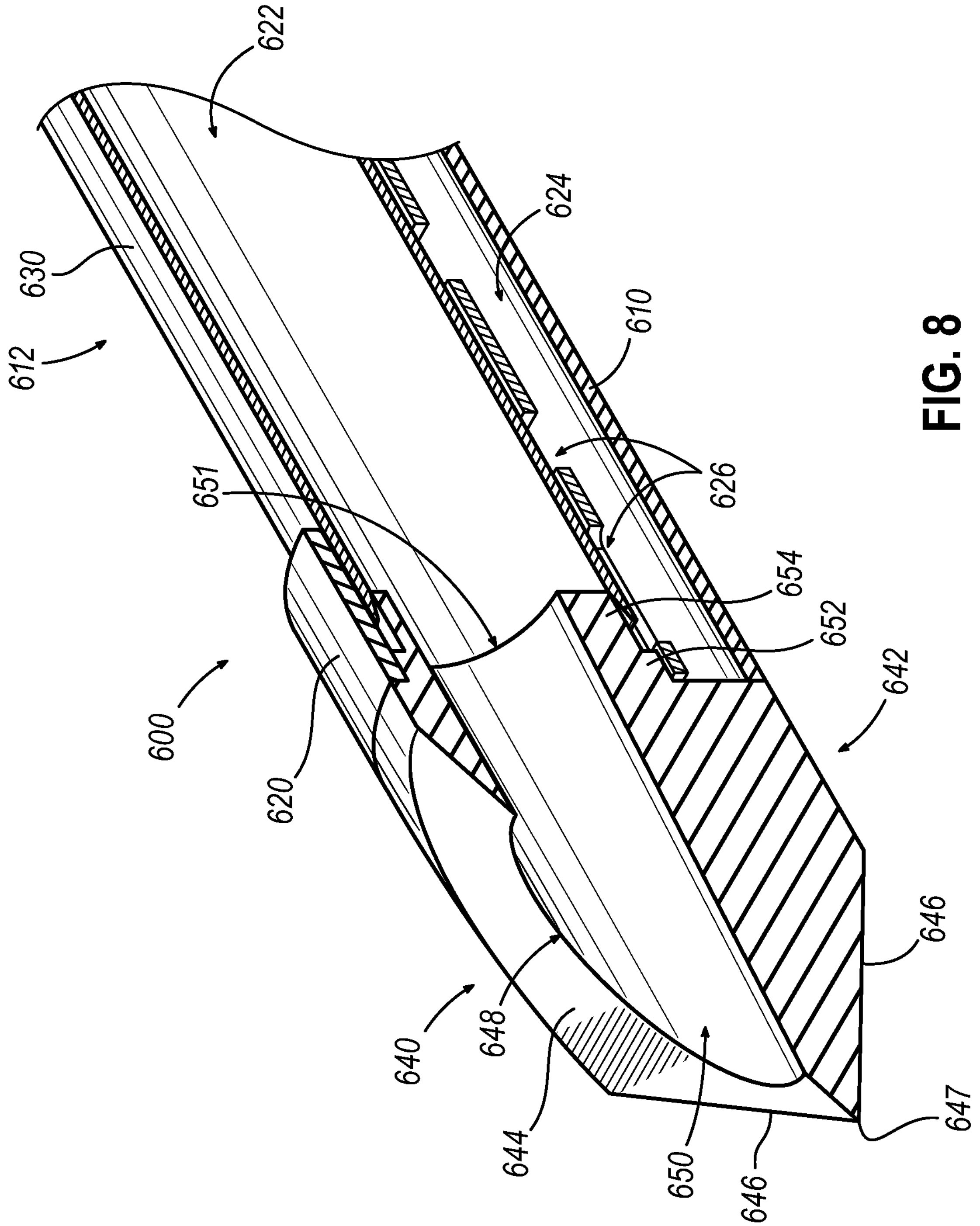
FIG. 8 depicts a perspective cross-sectional view of the biopsy needle of FIG. 5, the cross-section taken along line 8-8 of FIG. 5.

Outer cannula (610) includes a cutter receiving tube (620) received within a distal portion of outer cannula (610). Cutter receiving tube (620) defines lateral aperture (612) and is generally circular, while outer cannula (610) is oval-shaped. As best seen in FIG. 8, this configuration provides a two-lumen configuration, with an upper cutter lumen (622) and a lower lateral lumen (624). Both cutter lumen (622) and lower lumen (624) are in fluid communication by one or more fluid openings (626) disposed within a portion of cutter receiving tube (620) opposite of lateral aperture (612).

Cutter receiving tube (620) is generally configured to receive a tubular cutter (630). It should be understood that cutter (630) is generally configured to be movable within cutter receiving tube (620) relative to lateral aperture (612). In some examples, cutter (630) is moved proximally of lateral aperture to "open" lateral aperture (612). Tissue samples are then drawn into lateral aperture (612) by vacuum supplied though cutter lumen (622), lateral lumen (624), or both. Cutter (630) is then advanced distally to the position shown in FIG. 8 to sever a tissue sample. The severed tissue sample can then be transported though cutter (630) and into a tissue sample holder or other tissue receiving feature under vacuum supplied by the biopsy device.

Figure 6:
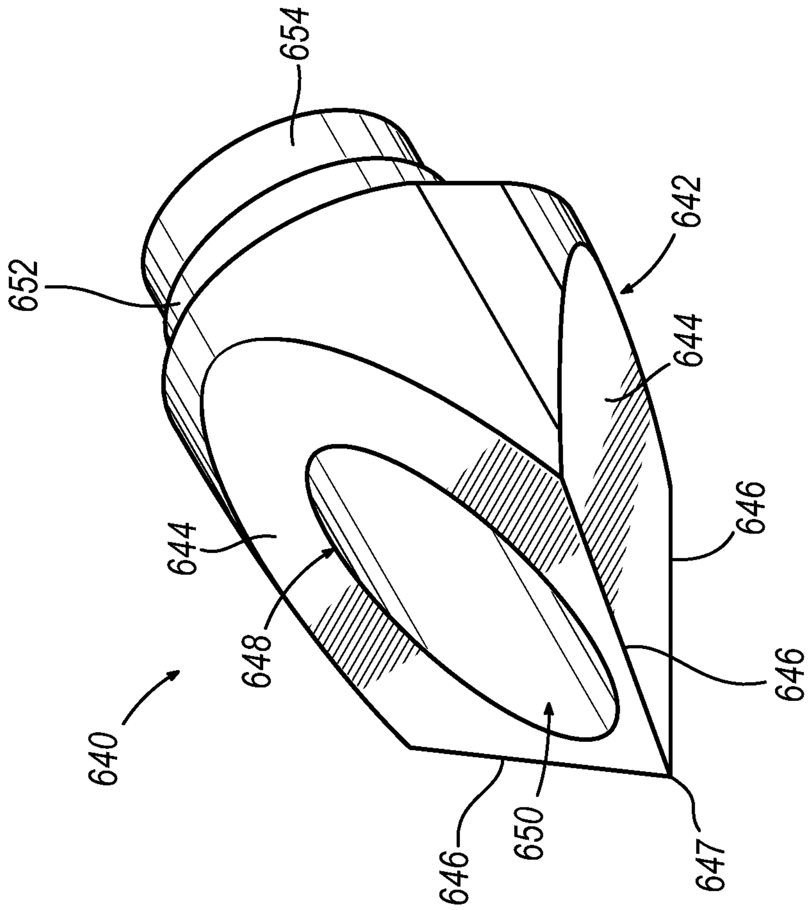
FIG. 6 depicts a detailed perspective view of a tissue piercing tip of the biopsy needle of FIG. 5.
Figure 7:
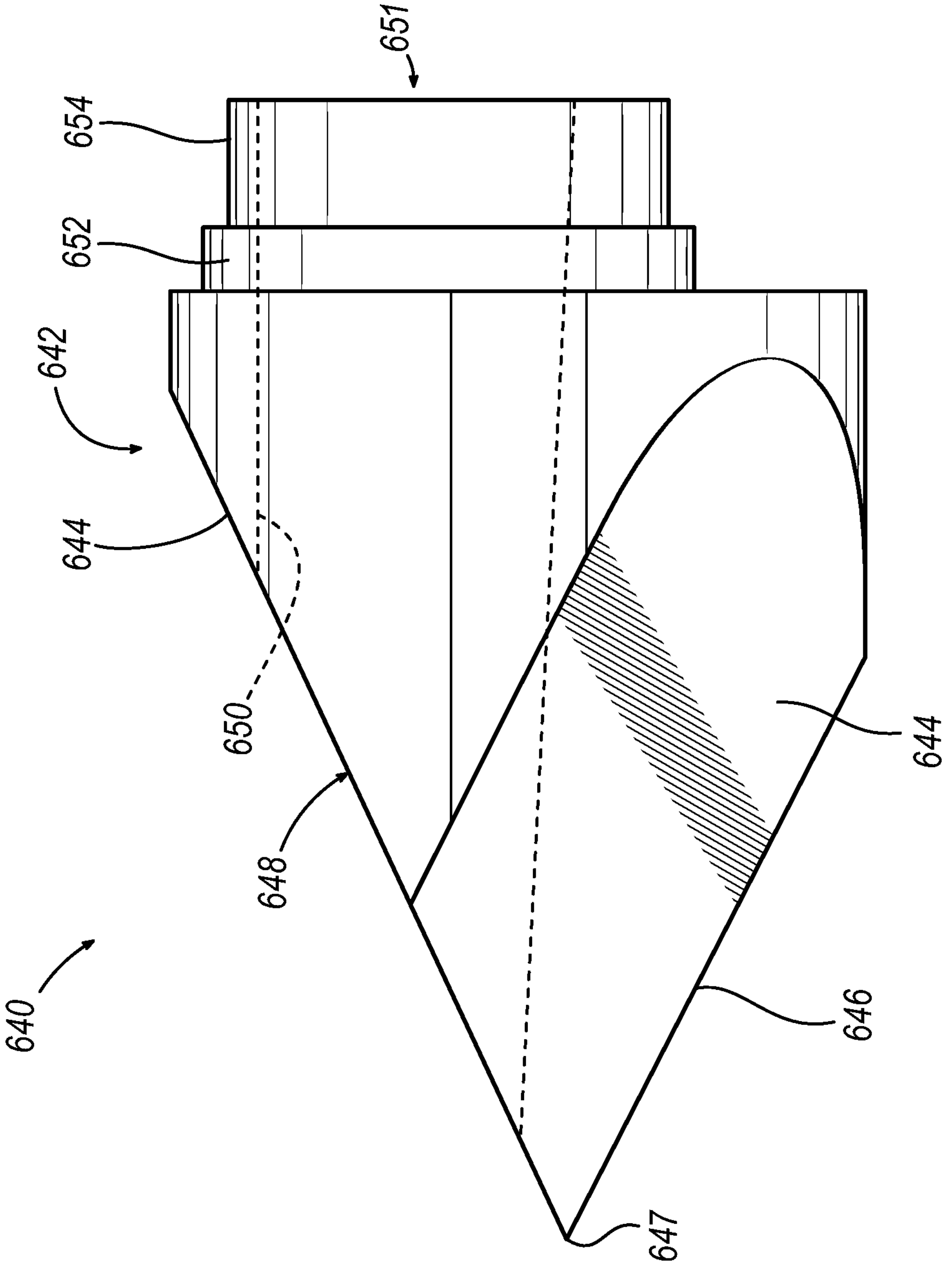
FIG. 7 depicts a side elevational view of the tissue piercing tip of FIG. 7.

Piercing tip (640) is best shown in FIGS. 6 and 7. As can be seen, piercing tip (640) includes a body (642) defining a plurality of cutting surfaces (644) on the distal end of piercing tip (640). In the present example, three cutting surfaces (644) are arranged around the exterior of body (642) to converge thereby forming a plurality of cutting edges (646). Cutting edges (646) similarly converge to form a sharp distal tip (647). Although surfaces (644) are referred to herein as "cutting surfaces," it should be understood that actual cutting of tissue can be performed by other structural elements. For instance, in the present example cutting edges (646) and sharp distal tip (647) actually perform cutting. Meanwhile, cutting surfaces (644) merely define the shape and or structure of cutting edges (646) and sharp distal tip (647). Thus, use of the term "cutting" herein in connection with the term "surface" does not necessarily imply that physical cutting of tissue is performed by such cutting surfaces (644).

Cutting surfaces (644) can be formed in the exterior of body (642) in a variety of ways. For instance, in some examples cutting surfaces (644) can be roughly formed by a molding technique such as metal injection molding. Next, cutting surfaces (644) can be further defined by cutting, grinding, abrading, or a combination thereof. In other examples, cutting surfaces (644) are formed entirely cutting, grinding, abrading, or a combination thereof. Still other techniques for forming cutting surfaces (644) will be apparent to those of ordinary skill in the art in view of the teachings herein.

Cutting surfaces (644) in the present example are generally flat. In other words, each cutting surface (644) lies within a single plane oriented at an angle relative to the longitudinal axis of body (642). Although each cutting surface (644) in the present example is shown as being oriented at a particular angle relative to the longitudinal axis of body (642), it should be understood that in other examples various alternative angles can be used as will be apparent to those of ordinary skill in the art in view of the teachings herein.

The proximal end of body (642) includes an intermediate end (652) and a proximal end (654) extending proximally from intermediate end (652). Intermediate end (652) and proximal end (654) both define a generally cylindrical shape. Additionally, intermediate end (652) and proximal end (654) are both oriented co-axially relative to each other. However, intermediate end (652) has a larger diameter relative to the diameter of proximal end (654) such that intermediate end (652) and proximal end (654) together form a progressively decreasing cross-section similar to a step formation.

Both intermediate end (652) and proximal end (654) are configured for receipt within at least a portion of outer cannula (610). For instance, as best seen in FIG. 8, intermediate end (652) is configured to directly abut an upper portion of the distal end of cutter receiving tube (620) while also being inside outer cannula (610). Meanwhile, proximal end (654) extends proximally past intermediate end (652) further into the interior of cutter receiving tube (620). Additionally, the diameter of proximal end (654) is generally undersized relative to the diameter of cutter receiving tube (620) to provide a space between cutter receiving tube (620) and the exterior of proximal end (654). This space is generally configured for receipt of at least a portion of cutter (630) to promote the severing of tissue.

In the present example, body (642) of tissue piercing tip (640) is coupled to outer cannula (610) and cutter receiving tube (620) by a welding process such as laser welding. In other examples, body (642) can be coupled to outer cannula (610) and/or cutter receiving tube (620) in a variety of ways such as by adhesive bonding, mechanical fastening, and/or compression fit.

As best seen in FIG. 6, body (642) further defines a distal opening (648) positioned on a single cutting surface (644). Distal opening (648) is generally oval-shaped and is in communication with a lumen (650) extending through body (642), as will be described in greater detail below. In the present example, distal opening (648) is positioned on the cutting surface (644) oriented upwardly (e.g., towards the top of the page in FIG. 6). However, it should be understood that in other examples, distal opening (648) can be positioned on any other cutting surface (644).

In the present example, distal opening (648) is positioned entirely within a single cutting surface (644) to generally avoid interaction between distal opening (648) and tissue while biopsy needle (600) is penetrating tissue. In such circumstances, that majority of the force between cutting surfaces (644) and tissue is directed towards cutting edges (646). Thus, as tissue piercing tip (640) penetrates tissue, such tissue will generally move over distal opening (648) rather than snagging or being abraded by distal opening (648).

Although distal opening (648) is described herein as being positioned entirely on a single cutting surface (644), it should be understood that in other examples distal opening (648) may be positioned across multiple cutting surfaces (644). For instance, in some examples, distal opening can be positioned adjacent to distal tip (647) and can thus intersect all three cutting surfaces (644). In such examples, the combination of distal tip (647) and cutting surfaces (644) may be similar to a hypodermic needle.

As will be described in greater detail below, distal opening (648) is generally configured to communicate a marker out of body (642). As such, it should be understood that the size or diameter of distal opening (648) generally corresponds to the size or diameter of a marker such as markers (100, 300) described above. Similarly, since distal opening (648) in the present example is positioned entirely on a single cutting surface (644), it should be understood that one or more cutting surfaces (644) can also be sized in proportion to the size or diameter of a marker. While being large enough to accommodate a marker, distal opening (648) is also small enough to generally prevent ingress of tissue. As will be described in greater detail below, this sizing permits distal opening (648) to self-seal using adjacent tissue when distal opening (648) is not in use for marker delivery.

As best seen in FIGS. 7 and 8, body (642) defines lumen (650) extending from distal opening (648) to proximal opening (651). The cross-sectional diameter or size of lumen (650) generally corresponds to the diameter of distal opening (648). Like with distal opening (648) described above, lumen (650) is generally sized to communicate a marker through body (642) from proximal opening (651) to distal opening (648). Although the cross-sectional diameter or size of lumen (650) of the present example is generally shown as being consistent along the length of body (642), it should be understood that in some examples the cross-sectional diameter or size of lumen (650) can vary along the length of body (642). For instance, in some examples the cross-sectional diameter or size of lumen (650) can taper inwardly as lumen (650) extends distally from proximal opening (651). In such examples, lumen (650) can thus act as a funnel to direct a marker into a desired position. Of course, other sizes and/or shapes of lumen (650) may be apparent to those of ordinary skill in the art in view of the teachings herein.

As best seen in FIG. 7, lumen (650) is oriented at a slight angle relative to the longitudinal axis of body (642). In particular, lumen (650) is angled such that lumen (650) extends upwardly as lumen (650) extends distally. In the present example, this angle is present to account for differences in orientation between distal opening (648) and proximal opening (651). By way of example only, the specific angle of lumen (650) in the present example is approximately 5°. However, it should be understood that in other examples the angle of lumen (650) can range between 2 and 10°. In still other examples, various other angles may be used depending on the particular size, shape, and geometry of tissue piercing tip (340).

Proximal opening (651) is defined by proximal end (654) of body (642). As best seen in FIG. 8, proximal opening (651) connects lumen (650) to the interior of needle (600). As will be described in greater detail below, this configuration permits a marker to be delivered through cutter (630) and into lumen (650). As such, it should be understood that proximal opening (651) is generally positioned to align with cutter (630). Additionally, proximal opening (651) defines a diameter or size that corresponds to the diameter or size of a marker such that proximal opening (651) is generally configured to receive a marker.

B. Exemplary Marker Delivery Device with End Deployment

Figure 9:
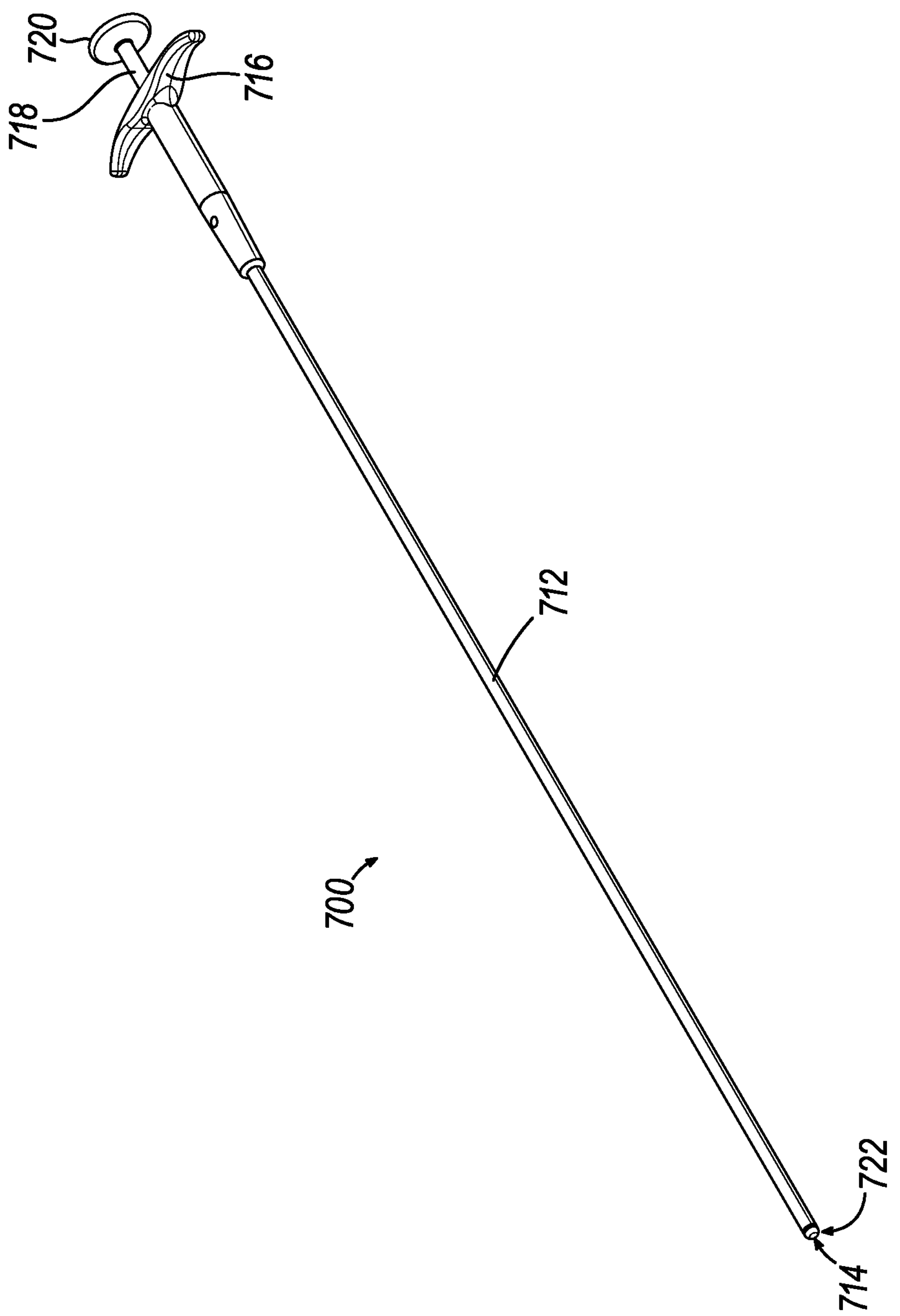
FIG. 9 depicts a perspective view of an exemplary marker delivery device for use with the biopsy needle of FIG. 5.
Figure 10:
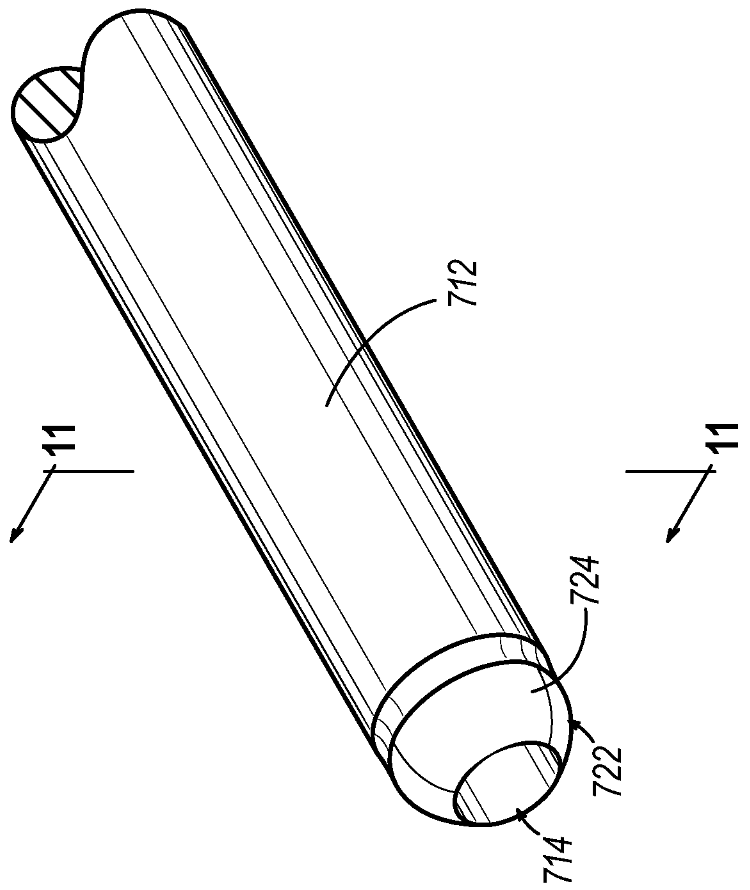
FIG. 10 depicts a detailed perspective view of a cannula of the marker delivery device of FIG. 9.
Figure 11:
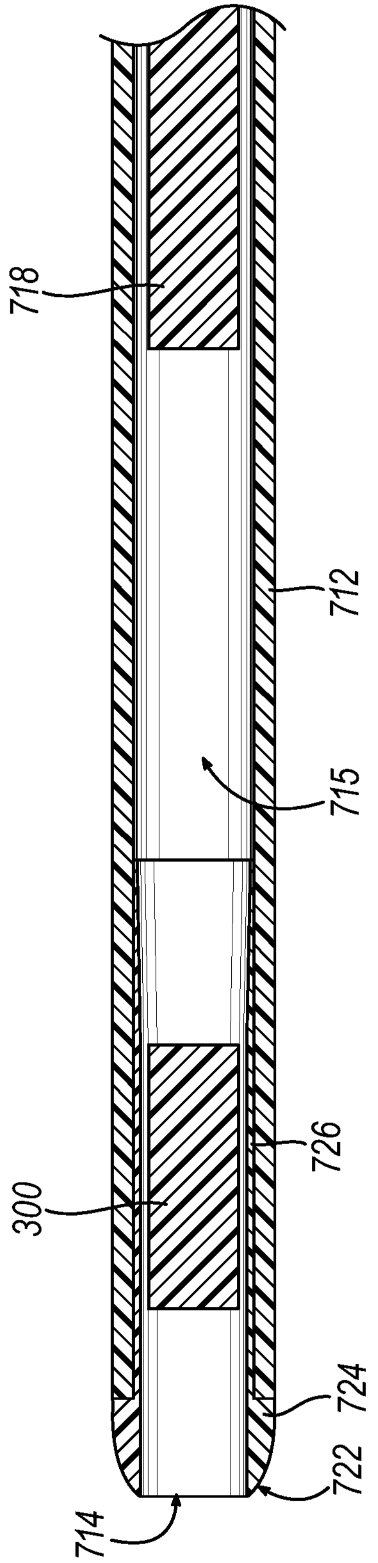
FIG. 11 depicts a detailed cross-sectional view of the cannula of FIG. 9, the cross-section taken along line 11-11 of FIG. 10.

FIGS. 9 through 11 show an exemplary marker delivery device (700) that can be used with needle (600) described above. As best seen in FIG. 9, marker delivery device (700) includes an elongate outer cannula (712) having a marker exit (714). Outer cannula (712) is generally sized to slidably fit within cutter (630) of needle (600). Similarly, the length of cannula (712) is generally sized to correspond to the length of needle (600). It should be understood that in some examples the particular length of cannula (712) can be greater than the length of needle (600). For instance, in some examples the proximal end of needle (600) and/or cutter (650) can be coupled to a tissue sample holder or other tissue collection device. In such examples, the length of cannula (712) can have a length suitable to extend through both needle (600)/cutter (650) and various tissue collection devices.

A grip (716) can be provided at the proximal end of cannula (712). A push rod (718) can be provided, with push rod (718) extending coaxially in cannula (712) such that push rod (718) is configured to translate within cannula (712) to displace one or more markers through marker exit (714). Push rod (718) generally has sufficient rigidity in compression to push a marker from an internal lumen (715) of cannula (712) out through marker exit (714), yet be relatively flexible in bending. A plunger (720) is coupled at the proximal end of push rod (718) for forcing push rod (718) distally in cannula (712) to deploy a marker out of cannula (712).

FIG. 10 depicts a detailed view of a distal end (722) of cannula (712). As can be seen, marker exit (714) is disposed in the center of distal end (722). Thus, it should be understood that marker exit (714) is generally positioned coaxially with internal lumen (715) of cannula (712). Accordingly, marker delivery device (700) of the present example is an “end-deploy” marker delivery device, rather than a “side-deploy” marker delivery device. As will be described in greater detail below, this configuration generally permits marker delivery device (700) to be used with needle (600) to deploy a marker from distal opening (648) in distal tip (647) rather than lateral aperture (612).

Distal end (722) is generally rounded relative to the outer diameter of cannula (712). Accordingly, it should be understood that distal end (722) generally tapers or rounds inwardly towards marker exit (714). As will be understood, this configuration generally avoids snagging of distal end (722) on various internal geometries of needle (600). Although distal end (722) is shown as being rounded, it should be understood that various other alternative geometries can be used such as frustoconical, tapered, and/or etc.

As best seen in FIG. 11, distal end (722) is shown as a separate component inserted into cannula (712). In particular, distal end (722) includes a distal tip (724) and an inert portion (726). Distal tip (724) defines the rounded portion of distal end (722) that is external to cannula (712). Insert portion (726) extends proximally from distal tip (724) and is disposed within cannula (712). Insert portion (726) defines a tapered diameter that is distally slightly oversized relative to the inner diameter of internal lumen (715). As insert portion (726) extends proximally away from distal tip (724), the diameter of insert portion (726) progressively decreases to being approximately equivalent to the inner diameter of internal lumen (715). This configuration generally provides a press fit arrangement between distal end (722) and cannula (712). Additionally, this configuration provides a gradual transition between cannula (712) and distal end (722) to prevent a marker from snagging at the transition. Although a press or mechanical fit is used in the present example, it should be understood that in other examples distal end (722) can be secured to cannula (712) using other fastening methods such as snap fits, adhesive bonding, welding, and/or etc. In still other examples, distal end (722) can be integral with cannula (712).

Marker delivery device (700) in the present example is shown equipped with marker (300). However, it should be understood that in other examples any suitable alternative markers can be used with marker delivery device (700). Marker (300) is initially disposed within cannula (712) distally of a distal end of push rod (718). Accordingly, it should be understood that push rod (718) can be advanced within cannula (712) to push marker (300) from marker exit (714). Although not shown, it should be understood that in some examples internal lumen (715) can be equipped with detents, internal ridges, rubber gaskets, or other similar features to hold marker (300) within cannula (712) until marker (300) is actuated out of marker exit (714) by push rod (718).

C. Exemplary Method for End Deployment of Biopsy Site Marker

Figure 12A:
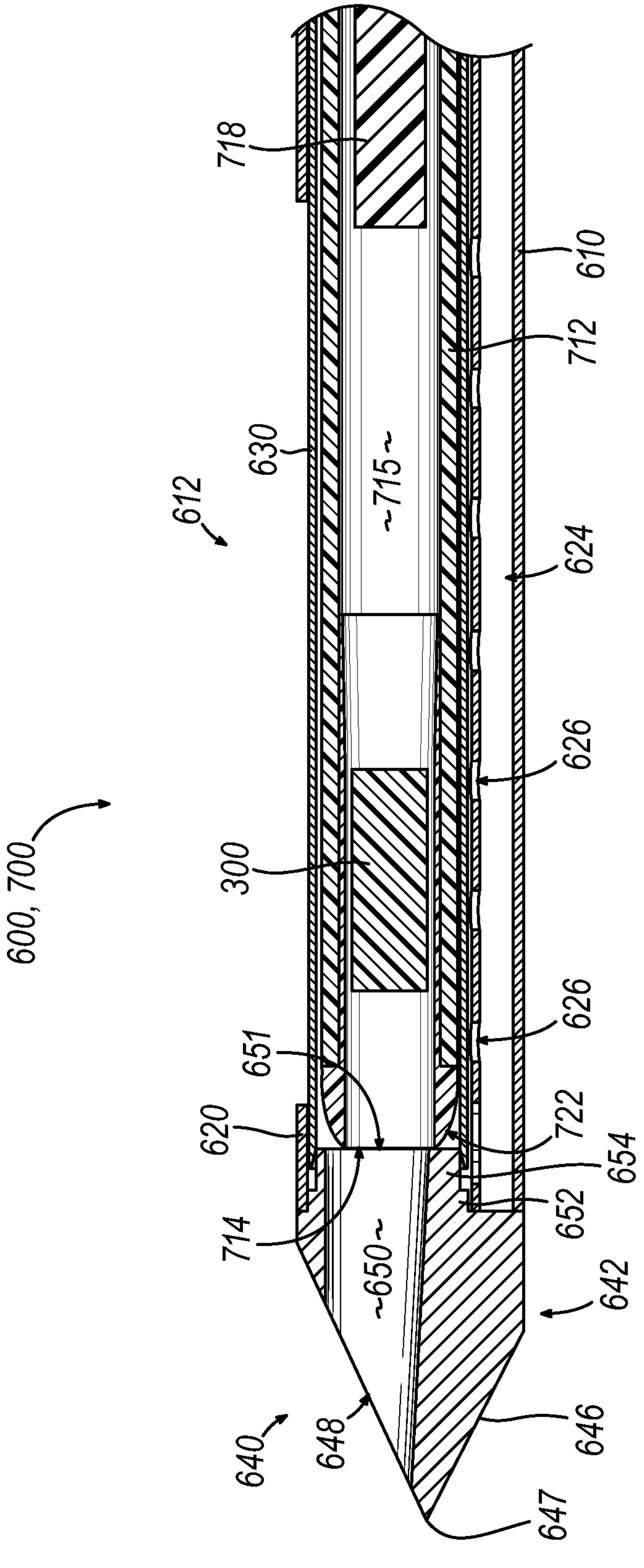
FIG. 12A delicts a side cross-sectional view of the biopsy needle of FIG. 5 and the cannula of FIG. 10, with the cannula inserted therein.
Figure 12B:
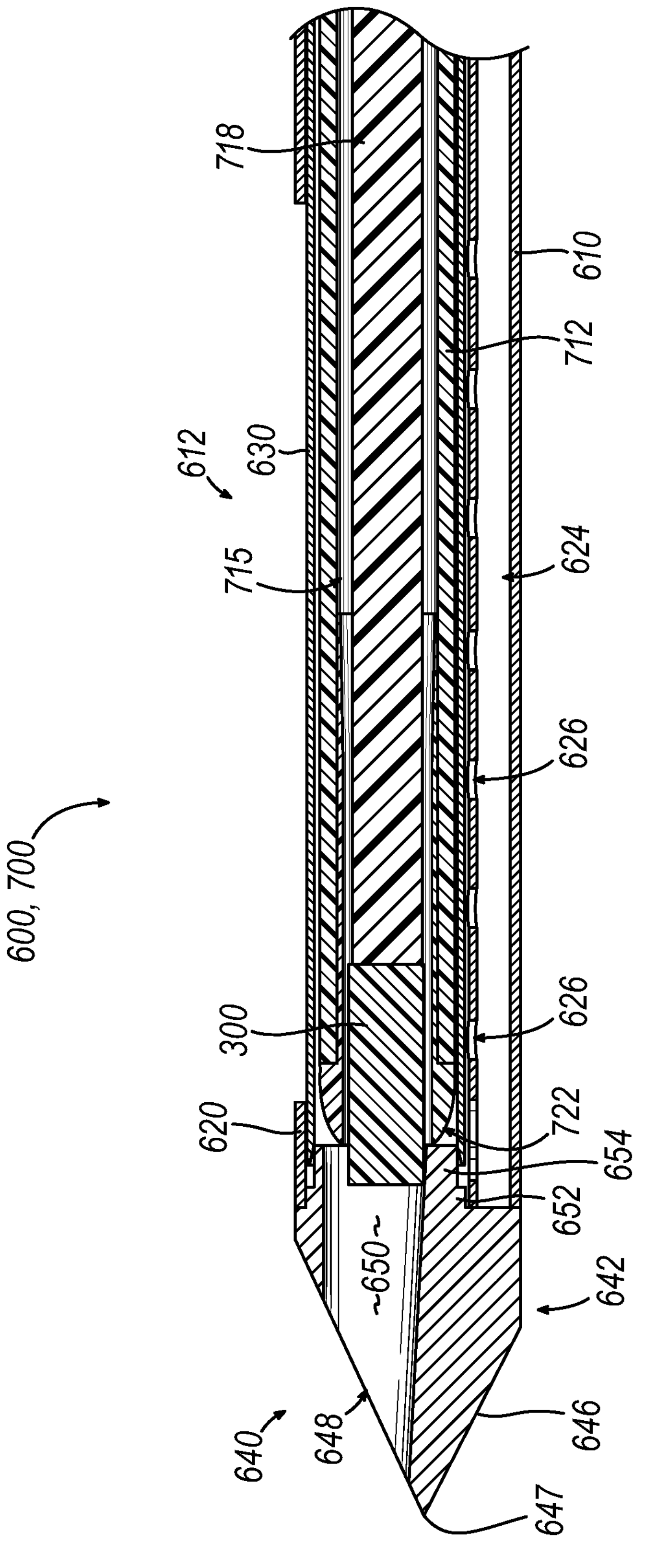
FIG. 12B depicts another side cross-sectional view of the biopsy needle of FIG. 5 and the cannula of FIG. 10, with the marker delivery device in an intermediate position.
Figure 12C:
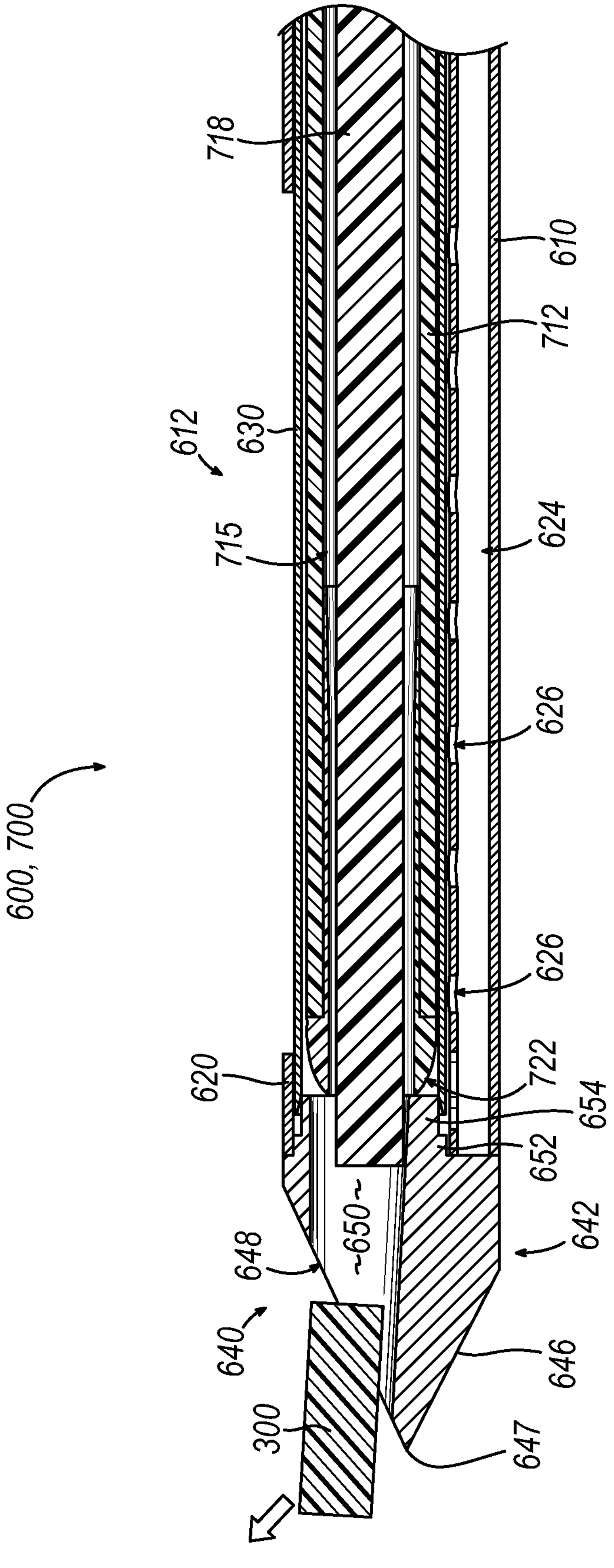
FIG. 12C depicts yet another side cross-sectional view of the biopsy needle of FIG. 5 and the cannula of FIG. 10, with the marker delivery device in a deployed position.

FIGS. 12A through 12C show an exemplary use of marker delivery device (700) with needle (600). As can be seen in FIG. 12A, cannula (712) of marker delivery device (700) is initially inserted into needle (600) through cutter (630). In particular, cannula (712) is inserted into needle (600) through cutter (630) until distal end (722) contacts proximal end (754) of tissue piercing tip (640). In this position, cannula (712) is coaxial with cutter (630). This aligns marker exit (714) with proximal opening (651) of tissue piercing tip (640).

Once cannula (712) is disposed within needle (600) as shown in FIG. 12A, maker delivery device (700) is positioned for deployment of marker (300). Thus, it should be understood that at this stage marker (300) is disposed within cannula (712). Similarly, push rod (718) is in a pre-actuated state corresponding to a proximal position within cannula (712).

Insertion of marker delivery device (700) into needle (600) for deployment of a marker may occur at a variety of stages during a biopsy procedure. For instance, in some examples, marker delivery device (700) can be inserted into needle (600) after the completion of a biopsy procedure while needle (600) is still disposed within a patient once all desired tissue samples have been collected from a given biopsy site. Alternatively, marker delivery device (700) can be inserted into needle (600) at one or more intermediate stages during a biopsy procedure. In yet other examples, marker delivery device (700) can be used at other stages where marking of a site of interest is desired. In addition, although not shown, it should be understood that insertion of marker delivery device (700) can be accompanied with other procedural steps such as adjusting a tissue sample holder, removing a tissue sample holder, or removing parts of a tissue sample holder, or removing other portions of a biopsy device.

Regardless of the particular stage of performing marking, it should be understood that in some examples needle (600) may require at least some repositioning relative to the biopsy site prior to marking. For instance, in the present example tissue samples are collected through lateral aperture (612) of needle (600). Meanwhile, marking occurs through distal opening (648), which is positioned away from lateral aperture (612). Thus, in some examples it may be desirable to reposition needle (600) to align distal opening (648) with the biopsy site that was initially positioned adjacent to lateral aperture (612).

Once cannula (712) is inserted into needle (600) an operator may desire to deploy marker (300) from marker delivery device (700). Deployment of marker (300) is shown in FIGS. 12B and 12C. As can be seen, deployment is initiated by advancing push rod (718) distally using plunger (720) or a combination of plunger (720) and grip (716). As shown in FIG. 12B, advancement of push rod (718) results in the distal end of push rod (718) engaging marker (300) to drive marker distally along with push rod (718).

As marker (300) is driven distally via push rod (718), marker (300) is pushed through internal lumen (715) of cannula (712), through distal end (722), and out of marker exit (714). Once marker (300) is pushed out of marker exit (714), marker enters lumen (650) of tissue piercing tip (640) via proximal opening (651). Since lumen (650) is oriented at an angle as described above, it should be understood that lumen (650) can align marker (300) to some extent along the axis of lumen (650).

As best seen in FIG. 12C, further advancement of push rod (718) causes marker (300) to proceed further through lumen (650) until marker (300) exits needle (600) entirely through distal opening (648) in tissue piercing tip (640). Although not shown, it should be understood that in some uses a distal portion of push rod (718) can also exit needle (600) through distal opening (648) to provide additional penetration of marker (300) into tissue. However, in other uses push rod (718) may alternatively remain within lumen (650) as shown in FIG. 12C.

Once marker (300) is deployed as shown in FIGS. 12A through 12C, marker delivery device (700) can be removed from needle (600). If additional marking is desired, marker delivery device (700) can be reloaded with an additional marker (300). Alternatively, an another identical or substantially identical marker delivery device (700) can be used for deployment of additional markers (300). If no additional marking is desired after deployment of marker (300), needle (600) can also be removed from the patient either in conjunction with removal of marker delivery device (700) or separately.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A needle for use with a biopsy device comprising: an outer cannula defining a cutter lumen for receiving a cutter therein and a lateral lumen adjacent to the cutter lumen; and a tissue piercing tip having body defining a plurality of cutting surfaces, a marker opening disposed on at least one cutting surface of the plurality of cutting surfaces, and a marker lumen extending distally through the body from the marker opening to a proximal opening, wherein the proximal opening is in communication with the cutter lumen.

Example 2

The needle of Example 1, wherein the marker opening is disposed on a single cutting surface of the plurality of cutting surfaces.

Example 3

The needle of Example 1, wherein the marker opening is disposed on a two or more cutting surfaces of the plurality of cutting surfaces.

Example 4

The needle of any one or more of Examples 1 through 3, wherein the proximal opening is coaxial with an axis defined by the cutter lumen.

Example 5

The needle of any one or more of Examples 1 through 4, wherein the marker lumen is disposed at an oblique angle relative to a central axis of the outer cannula.

Example 6

The needle of any one or more of Examples 1 through 5, wherein marker lumen is sized to receive a marker therein.

Example 7

The needle of any one or more of Examples 1 through 6, wherein the marker lumen is sized to prevent the prolapse of tissue therein.

Example 8

The needle of any one or more of Examples 1 through 7, wherein the each cutting surface of the plurality of cutting surfaces converge to form one or more cutting edges.

Example 9

The needle of any one or more of Examples 1 through 8, wherein the cutter defines a lumen configured to receive a cannula of a marker delivery device such that the marker delivery device can be received in the cutter to deploy a marker through the marker lumen.

Example 10

A biopsy system comprising: a biopsy device including body, a needle extending distally from the body, and a cutter movable relative to the needle, wherein the needle includes an outer cannula, a tissue piercing tip secured to a distal end of the outer cannula, and a cutter lumen configured to receive the cutter, wherein the tissue piercing tip defines a marker lumen in communication with the exterior of the cutter and the cutter lumen; a marker delivery device including an elongate cannula having a distal end with a marker exit disposed in the distal end; and a biopsy site marker, wherein the marker delivery device is configured to expel the biopsy site marker through the marker exit and out of the needle through the maker lumen defined by the tissue piercing tip.

Example 11

The biopsy system of Example 10, wherein the elongate cannula of the marker delivery device is configured for insertion into the cutter of the biopsy device.

Example 12

The biopsy system of any one or more of Examples 10 and 11, wherein the distal end of the marker delivery device defines a rounded distal tip.

Example 13

The biopsy system of Example 12, wherein the marker exit is centered within the rounded distal tip.

Example 14

The biopsy system of any one or more of Examples 10 through 13, wherein the tissue piercing tip further defines a plurality of cutting surfaces, wherein the marker lumen extends through a single cutting surface of the plurality of cutting surfaces.

Example 15

The biopsy system of any one or more of Examples 10 through 13, wherein the tissue piercing tip further defines a plurality of cutting surfaces, wherein the marker lumen extends through a two or more cutting surfaces of the plurality of cutting surfaces.

Example 16

The biopsy system of any one or more of Examples 10 through 15, wherein the cutter is configured to align the marker exit of the marker delivery device with the marker lumen of the tissue piercing tip.

Example 17

The biopsy system of any one or more of Examples 10 through 16, wherein the needle further includes a cutter receiving tube configured to receive the cutter, wherein the cutter receiving tube and the outer cannula together define a lateral lumen positioned below the cutter.

Example 18

The biopsy system of any one or more of Examples 10 through 17, further comprising a tissue sample holder in communication with the cutter and configured to receive one or more tissue samples severed by the cutter, wherein the tissue sample holder is configured to receive the elongate cannula of the marker delivery device for marking purposes through the cutter.

Example 19

The biopsy system of any one or more of Examples 10 through 18, wherein the marker lumen extends through the tissue piercing tip at an angle relative to a central longitudinal axis of the needle.

Example 20

The biopsy system of any one or more of Examples 10 through 18, wherein the marker lumen extends through the tissue piercing tip at an angle relative to a central longitudinal axis of the needle such that the marker lumen projects upwardly as the marker lumen extends distally through the tissue piercing tip.

Example 21

A method for marking a biopsy site comprising: positioning a biopsy needle proximate a biopsy site; collecting one or more tissue samples from the biopsy site by moving a cutter relative to the needle; inserting a marker delivery device into the needle through the cutter; and expelling a marker from the marker delivery device towards the biopsy site through a marker lumen in a tissue piercing tip of the needle.

Example 22

The method of Example 21, further comprising repositioning the biopsy needle to align the marker lumen with the biopsy site.

Example 23

The method of Example 22, wherein the step of expelling the marker is performed by advancing a push rod through a cannula of the marker delivery device.

Example 24

The method of any one or more of Examples 21 through 23, wherein the step of collecting one or more tissue samples includes prolapsing tissue through a lateral aperture in the biopsy needle.

Example 25

The method of any one or more of Examples 21 through 24, wherein the step of inserting the marker delivery device into the needle includes inserting the marker delivery device into a tissue sample holder to access the cutter.

V. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A biopsy system comprising:

(a) a biopsy device including a body, a needle extending distally from the body, and a tubular cutter movable relative to the needle, wherein the needle includes an outer cannula, a tissue piercing tip secured to a distal end of the outer cannula, and a cutter receiving tube configured to receive the tubular cutter, wherein the tissue piercing tip defines a marker lumen in communication with an exterior of the tubular cutter and the cutter receiving tube;

(b) a marker delivery device including an elongate cannula having a distal end with a marker exit disposed in the distal end; and (c) a biopsy site marker, wherein the marker delivery device is configured to expel the biopsy site marker through the marker exit and out of the needle through the marker lumen defined by the tissue piercing tip, wherein the tubular cutter is configured to receive the elongate cannula of the marker delivery device from a proximal end of the tubular cutter during use of the marker delivery device and the tubular cutter further defining a continuous path allowing removal of the elongate cannula after use, wherein the tissue piercing tip comprises a plurality of cutting surfaces which converge to form a sharp distal tip at a point, wherein the marker lumen projects at an oblique angle away from the elongate cannula towards at least one cutting surface, wherein another at least one cutting surface is offset from elongate cannula.

2. The biopsy system of claim 1, wherein the marker lumen extends through a single cutting surface of the plurality of cutting surfaces.

3. The biopsy system of claim 1, wherein the marker lumen extends through two or more cutting surfaces of the plurality of cutting surfaces.

4. The biopsy system of claim 1, wherein the tubular cutter is configured to align the marker exit of the marker delivery device with the marker lumen of the tissue piercing tip.

5. The biopsy system of claim 1, wherein the cutter receiving tube and the outer cannula together define a lateral lumen positioned below the tubular cutter.

6. The biopsy system of claim 1, further comprising a tissue sample holder in communication with the tubular cutter and configured to receive one or more tissue samples severed by the tubular cutter, wherein the tissue sample holder is configured to receive the elongate cannula of the marker delivery device through the tubular cutter.

7. The biopsy system of claim 1, wherein the tubular cutter of the biopsy device is hollow.

8. The biopsy system of claim 7, wherein the tubular cutter of the biopsy device is situated within the needle.

9. A biopsy system comprising:

(a) a biopsy device including a body, a needle extending distally from the body, and a cutter movable relative to the needle, wherein the cutter is hollow, wherein the needle includes an outer cannula, a tissue piercing tip secured to a distal end of the outer cannula, and a cutter lumen configured to receive the cutter, wherein the tissue piercing tip defines a marker lumen in communication with an exterior of the cutter and the cutter lumen, wherein the tissue piercing tip further defines a plurality of cutting surfaces, wherein the marker lumen extends through at least one of the plurality of cutting surfaces of the tissue piercing tip at an oblique angle of 2 or more degrees relative to a central longitudinal axis of the needle such that the marker lumen projects from the central longitudinal axis toward the at least one of the plurality of cutting surfaces as the marker lumen extends distally through the tissue piercing tip;

(b) a marker delivery device including an elongate cannula having a distal end with a marker exit disposed in the distal end, the marker delivery device being insertable into the needle through a proximal opening in the needle, and through the cutter; and (c) a biopsy site marker, wherein the marker delivery device is configured to be advanced through the cutter past a distal end of the cutter until the marker delivery device is in communication with the marker lumen of the tissue piercing tip to expel the biopsy site marker through the marker exit and out of the needle through the marker lumen defined by the tissue piercing tip.

10. The biopsy system of claim 9, wherein the elongate cannula of the marker delivery device is configured for insertion into the cutter of the biopsy device.

11. The biopsy system of claim 9, wherein the marker lumen extends through a single cutting surface of the plurality of cutting surfaces.

12. The biopsy system of claim 9, wherein the marker lumen extends through two or more cutting surfaces of the plurality of cutting surfaces.

13. The biopsy system of claim 9, wherein the cutter of the biopsy device is received in a space between an outer cutter receiver tube and the proximal end of the tissue piercing tip.

14. A biopsy system comprising:

(a) a biopsy device including a body, a needle extending distally from the body, and a hollow cutter movable relative to the needle, wherein the needle includes an outer cannula, a tissue piercing tip secured to a distal end of the outer cannula, and a cutter lumen configured to receive the hollow cutter, wherein the tissue piercing tip includes a plurality of planar cutting surfaces, wherein the tissue piercing tip further includes a hollow lumen which extends at an oblique angle between 2 and 10 degrees from the central longitudinal axis of the needle through at least one of the plurality of planar cutting surfaces and is in communication with an exterior of the hollow cutter and the cutter lumen, and wherein a continuous path in the biopsy device is defined by a proximal opening in the body, extending through the body, the hollow cutter, and the hollow lumen of the tissue piercing tip;

(b) a marker delivery device including an elongate cannula having a distal end with a marker exit disposed in the distal end; and (c) a biopsy site marker, wherein the marker delivery device is configured to be inserted and directed through the continuous path of the biopsy device and to expel the biopsy site marker through the marker exit and out of the needle through the hollow lumen defined by the tissue piercing tip.

15. The biopsy system of claim 14, wherein the hollow lumen is configured to receive biopsy samples and deposit the biopsy site marker.

16. The biopsy system of claim 14, wherein the elongate cannula of the marker delivery device is configured for insertion into the hollow cutter of the biopsy device.

17. The biopsy system of claim 14, wherein the hollow lumen is centered within the tissue piercing tip.

* * * * *